US008883861B2

(12) United States Patent
Kohn et al.

(10) Patent No.: US 8,883,861 B2
(45) Date of Patent: Nov. 11, 2014

(54) IMINIC MONOMERS AND POLYMERS THEREOF

(75) Inventors: Joachim B. Kohn, Piscataway, NJ (US); Durgadas Bolikal, Edison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 251 days.

(21) Appl. No.: 13/287,008

(22) Filed: Nov. 1, 2011

(65) Prior Publication Data

US 2012/0108677 A1 May 3, 2012

Related U.S. Application Data

(60) Provisional application No. 61/408,697, filed on Nov. 1, 2010.

(51) Int. Cl.
| | |
|---|---|
| A61K 31/08 | (2006.01) |
| A61L 27/14 | (2006.01) |
| C08G 64/12 | (2006.01) |
| C08G 64/42 | (2006.01) |
| C08G 69/48 | (2006.01) |
| C08G 64/24 | (2006.01) |
| A61L 31/16 | (2006.01) |
| A61L 31/04 | (2006.01) |
| A61L 27/54 | (2006.01) |
| C07D 241/18 | (2006.01) |
| A61K 47/34 | (2006.01) |
| A61K 9/00 | (2006.01) |

(52) U.S. Cl.
CPC .............. *C08G 64/12* (2013.01); *A61L 27/14* (2013.01); *C08G 64/42* (2013.01); *A61K 47/34* (2013.01); *C08G 69/48* (2013.01); *C08G 64/24* (2013.01); *A61L 31/16* (2013.01); *A61L 31/04* (2013.01); *A61L 27/54* (2013.01); *C07D 241/18* (2013.01); *A61K 9/0024* (2013.01)
USPC ...................................................... 514/772.3

(58) Field of Classification Search
None
See application file for complete search history.

(56) References Cited

U.S. PATENT DOCUMENTS

| | | |
|---|---|---|
| 4,980,449 A | 12/1990 | Kohn et al. |
| 5,099,060 A | 3/1992 | Kohn et al. |
| 5,216,115 A | 6/1993 | Kohn et al. |
| 5,219,564 A | 6/1993 | Zalipsky et al. |
| 5,587,507 A | 12/1996 | Kohn et al. |
| 5,658,995 A | 8/1997 | Kohn et al. |
| 5,660,822 A | 8/1997 | Poiani et al. |
| 5,670,602 A | 9/1997 | Kohn et al. |
| 5,912,225 A | 6/1999 | Mao et al. |
| 6,103,255 A | 8/2000 | Levene et al. |
| 6,120,491 A | 9/2000 | Kohn et al. |
| 6,238,687 B1 | 5/2001 | Mao et al. |
| 6,284,862 B1 | 9/2001 | Kohn et al. |
| 6,475,477 B1 | 11/2002 | Kohn et al. |
| 6,602,497 B1 | 8/2003 | Kohn et al. |
| 2005/0106119 A1 | 5/2005 | Brandom et al. |
| 2006/0034769 A1 | 2/2006 | Kohn et al. |

OTHER PUBLICATIONS

Sung et al (Euro Cells and Materials 15:77-87, 2008).*
Gutowska et al., "Heparin release from therosensitive polymer coatings: In vivo studies," J. Biomater. Res., 29, 811-21 (1995).
Hoffman, "Applications of Thermally Reversible Polymers and Hydrogels in Therapautics and Diagnostics," J. Controlled Release, vol. 6, pp. 297-305 (1987).
Kaleta et al., "Thionation Using Fluorous Lawesson's Reagent," Org. Lett., 8(8), 1625-1628 (2006) (abstract only).
Kjaer, "Thioacylamido Acid Amides and Their Reactions with Mercuric Acetate," Acta Chemica Scandinavica, vol. 6, pp. 1374-1383 (1952).
Laurencin et al., "Poly(anhydride) administration in high doses in vivo: studies of biocompatibility and toxicology," J. Biomed. Mater. Res., vol. 24, pp. 1463-81 (1990) (abstract only).
Mikos et al., "Laminated three-dimentional biodegradable foams for use in tissue engineering," Biomaterials, vol. 14, pp. 323-329 (1993) (abstract only).
Nathan et al., "Copolymers of Lysine and Polyethylene Glycol: A New Family of Functionalized Drug Carriers," Bio. Cong. Chem., vol. 4, pp. 54-62 (1993).
Nathan et al., "Hydrogels Based on Water-Soluble Poly(ether urethanes) Derived from L-Lysine and Poly(ethylene glycol)," Macromolecules, vol. 25, pp. 4476-4484 (1992).
Schugens et al., "Polylactide macroporous biodegradable implants for cell transplantation. II. Preparation of polylactide foams by liquid-liquid phase separation," J. Biomed. Mater. Res., vol. 30, pp. 449-462 (1996) (Abstract only).
Urry et al., "Properties and Prevention of Adhesions Applications of Bioelestic Materials," Mat. Res. Soc. Symp. Proc., vol. 292, pp. 253-264 (1993).

\* cited by examiner

*Primary Examiner* — Craig Ricci
(74) *Attorney, Agent, or Firm* — Fox Rothschild LLP

(57) ABSTRACT

Disclosed are biocompatible, bioresorbable polymers comprising a plurality of monomeric repeating units containing an imine group, wherein the inclusion of said imine group is effective to lower the melt viscosity, the solution viscosity, or both, compared to the same polymer without an imine group.

4 Claims, No Drawings

IMINIC MONOMERS AND POLYMERS THEREOF

CROSS-REFERENCE TO RELATED APPLICATIONS

This application claims the benefit of priority under 35 U.S.C. §119(e) of U.S. Provisional Application Ser. No. 61/408,697, filed on Nov. 1, 2010, then entire disclosure of which is incorporated by reference herein.

BACKGROUND OF THE INVENTION

1. Field of the Invention

This invention relates to monomers and polymers containing imine functional groups (also known as Schiff bases), methods of making such monomers and polymers, and methods of using them in various applications, such as medical devices.

2. Description of the Related Art

Biodegradable polymers are widely used in the medical and pharmaceutical industries. When determining whether a polymer is suitable for use in these industries, the most important things to consider are the hydrolytic and thermal stability of said polymer. Other characteristics of a suitable polymer include said polymer being flexible, hydrophilic, degradable, non-immunogenic, additive compatible and non-toxic.

The tyrosine-derived monomers of U.S. Pat. No. 5,099,060 polymerize to form polymers with higher melt or solution viscosities that may result in poor processibility. As a result, the fabrication of the polymers requires higher temperatures, higher pressures, or both, which are less economical and may also degrade the polymer or any additives (such as biological or pharmaceutical moieties).

Such higher melt or solution viscosities can occur with tyrosine-derived polymers such as the polyiminocarbonates of U.S. Pat. No. 4,980,449, the polycarbonates of U.S. Pat. No. 5,099,060, the polyarylates of U.S. Pat. No. 5,216,115, the poly(alkylene oxide) block copolymers of U.S. Pat. No. 5,658,995, the phosphorous-containing polymers of U.S. Pat. Nos. 5,912,225 and 6,238,687, the anionic polymers of U.S. Pat. No. 6,120,491, the poly(amide carbonates) and poly(ester amides) of U.S. Pat. No. 6,284,862, the radio-opaque polymers of U.S. Pat. No. 6,475,477, and the polyethers of U.S. Pat. No. 6,602,497. The disclosures of all the foregoing patents are incorporated herein by reference in their entirety.

There exists a need for polymers with lower melt viscosities that are capable of being melt-processed and/or solution processed with greater ease, lower temperatures and/or pressures.

SUMMARY OF THE INVENTION

It was previously discovered that the amide bonds present in tyrosine-derived biocompatible polymers are involved in inter-chain hydrogen bonding, which can interfere in the thermal processibility of the polymer because hydrogen bonding between polymer chains increases melt or solution viscosity. In turn this led to the discovery that the effect due to hydrogen bonding in monomers and polymers with peptide linkages can be significantly reduced by replacing the hydrogen atom on the amide nitrogen with methyl or other alkyl groups.

It has now been discovered that converting the amides present in tyrosine-derived biocompatible polymers to imines as described herein produces polyimines with better glass transition temperatures, processing temperatures, and/or melt viscosity profiles than the corresponding polymers containing amides. According to at least one embodiment, polymers containing amide groups are reacted with phosgene or triphosgene in pyridine to form polyimines.

It has surprisingly been discovered that converting amide groups to imines eliminates or greatly reduces this source of intermolecular interaction to a degree such that polymer solubility in organic solvents increases, melt viscosity decreases, and the polymer glass transition temperature likewise decreases. These changes in polymer properties can be so profound that some polymers that were initially non-processible can now be processed by a variety of fabrication technologies, including solvent casting, wet and melt spinning, compression molding, extrusion, and injection molding.

Consequently, imine-containing versions of a polymer may be processed at lower temperatures (e.g., relative to the polymer glass transition temperature or $T_g$) with less thermal/oxidative degradation. This opens the temperature of processing window for polymers, e.g., higher $T_g$ polymers can be processed at existing process temperatures and similar $T_g$ polymers may be processed at lower temperatures.

Likewise, polymers solvated in relatively non-polar solvents, such as dichloromethane, can be processed at higher solids concentrations with lower solution viscosities.

Therefore, according to one embodiment, biocompatible, bioresorbable polymers are provided comprising a plurality of monomeric repeating units containing an imine group, linking within the polymer carbonyl or thiocarbonyl groups to carbon atoms substituted with carboxylate groups.

According to another embodiment, conversion of the amides to the imines is achieved to the extent sufficient to reduce either glass transition temperature, melt viscosity or processing temperature by at least about 5%, preferably at least about 10%. In yet another embodiment, replacing about 20% of the amides present in tyrosine-derived biocompatible polymers with imines is preferred. Replacing at least 50% of the amides with imines is more preferred. Most preferred is replacing about 75% of the amides present in tyrosine-derived polymers with imines.

In another embodiment, methods of preparing imine-containing polymers are disclosed. According to one embodiment, polymers with amides within a plurality of repeating units are transformed into polymers with imines within a plurality of repeating units by reacting the amide polymer with phosgene or triphosgene in pyridine, so that the resultant polymer exhibits a reduced melt processing temperature.

The following reaction scheme depicts a method for preparing the polymer with imines within a plurality of repeating units using poly (desaminotyrosyl-tyrosine) carbonate ethyl ester:

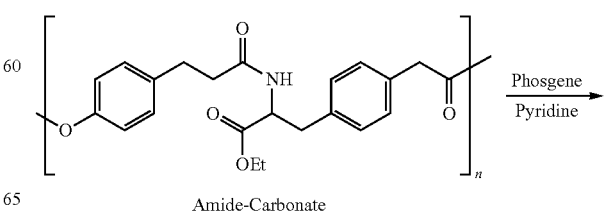

Amide-Carbonate

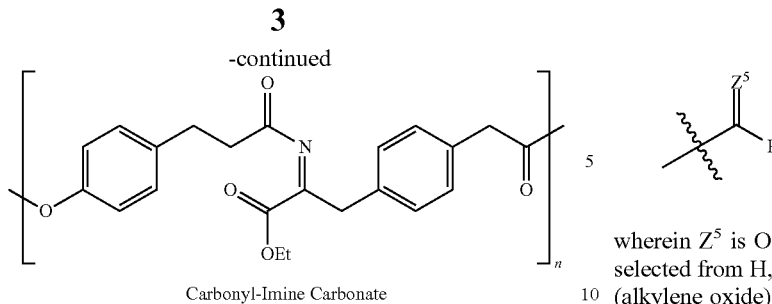

Carbonyl-Imine Carbonate

Another embodiment includes methods for preparing polyimines by reacting amide-containing monomers that polymerize upon reaction with phosgene with excess amounts of phosgene or triphosgene so that the phosgene or triphosgene both polymerizes the monomer to form a polycarbonate or analog thereof and converts the amide within the monomer, now a monomeric repeating unit, to an imine.

In another embodiment, imine monomers are prepared from amide monomer precursors by first protecting any groups that react with phosgene or triphosgene and then reacting the monomer with an amount of phosgene or triphosgene effective to convert the monomer amide to an imine.

According to another embodiment, polymers are provided with one or more recurring units of formula (I):

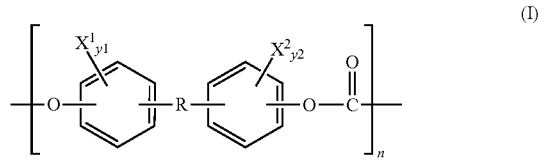

wherein $X^1$ and $X^2$ are each independently selected from Br and I; y1 and y2 are each independently zero or an integer in the range of 1 to 4, and $R^1$ is selected from the group consisting of substituted or unsubstituted, saturated or unsaturated, straight chain or branched aliphatic groups containing up to 48 carbon atoms, substituted or unsubstituted aromatic groups containing up to 48 carbon atoms, and substituted or unsubstituted araliphatic groups containing up to 48 carbon atoms in which the aliphatic portions are straight chain or branched and saturated or unsaturated, and $R^1$ contains from 4 to 8 heteroatoms selected from O, S and N, at least one of which in an imine nitrogen.

According to one embodiment, $R^1$ has a pendant carboxylic acid group or a pendant carboxylic acid ester group attached to the imino carbon.

According to another embodiment, $R^1$ in formula (I) is:

in which $R^{13}$ and $R^{14}$ each independently contain from 0 to 8 carbons atoms, inclusive, and are independently selected from $(-CHR^1)_e-CH=CH-(CHR^1)_e$ and $(-CHR^1)_f(-CHQ^2)_g(-CHR^1)_f$ each e independently ranges between 0 and 6, inclusive, each f independently ranges between 0 and 8, inclusive and g is 0 or 1; $Q^1$ is

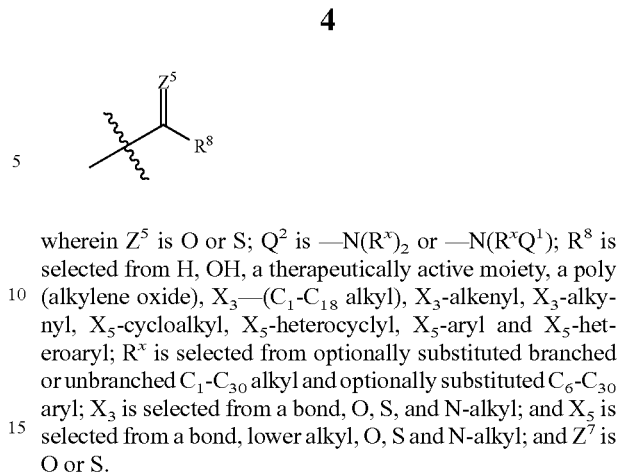

wherein $Z^5$ is O or S; $Q^2$ is $-N(R^x)_2$ or $-N(R^xQ^1)$; $R^8$ is selected from H, OH, a therapeutically active moiety, a poly(alkylene oxide), $X_3-(C_1-C_{18}$ alkyl), $X_3$-alkenyl, $X_3$-alkynyl, $X_5$-cycloalkyl, $X_5$-heterocyclyl, $X_5$-aryl and $X_5$-heteroaryl; $R^x$ is selected from optionally substituted branched or unbranched $C_1-C_{30}$ alkyl and optionally substituted $C_6-C_{30}$ aryl; $X_3$ is selected from a bond, O, S, and N-alkyl; and $X_5$ is selected from a bond, lower alkyl, O, S and N-alkyl; and $Z^7$ is O or S.

Alkyl, alkenyl, alkynyl, cycloalkyl, heterocyclyl, aryl and heteroaryl groups, except when otherwise defined, contain up to 30 carbon atoms. According to an embodiment, the groups contain up to 18 carbon atoms. Lower alkyl groups, except when otherwise defined, are straight or branched and contain up to 6 carbon atoms. Alkyl, alkenyl and alkynyl, groups are also straight or branched and contain from 0 to eight heteroatoms, and lower alkyl groups also contain 0, 1 or 2 heteroatoms. Heteroatoms are independently selected from O, S and N-lower alkyl. Heterocyclyl and heteroaryl groups also contain from one to eight heteroatoms selected from O, S and N-lower alkyl.

According to one embodiment the poly(alkylene oxide) $R^8$ groups include alkyl-terminated poly(alkylene oxides) of molecular weight 100 to 10,000, examples of which include methoxy-terminated poly(ethylene glycols) (PEG), methoxy-terminated poly(propylene glycols) (PPG), and methoxy-terminated block copolymers of PEG and PPG. According to another embodiment poly(alkylene oxide) groups have a molecular weight between about 400 and about 4000. According to another embodiment the poly(alkylene oxides) are poly(ethylene glycols) with molecular weights between about 1000 and about 2000.

According to another embodiment, one or both aromatic rings may be substituted with from 1 to 4 groups independently selected from halogen, lower alkyl, carboxyl, nitro, thioether, sulfoxide and sulfonyl. Any combination of substituents containing more than two nitro groups on one aromatic ring is potentially explosive, and is expressly excluded from these teachings. Monomers and polymers with a sufficient number of aromatic rings sufficiently substituted with bromine or iodine are inherently radio-opaque. In preferred radio-opaque monomers and polymers, at least one monomeric aromatic ring is substituted with iodine, so that the sum of y1 and y2 in formula (I) is greater than zero, preferably on at least one and more preferably on both ring positions ortho to the phenolic oxygen. Preferably both aromatic rings are iodine-substituted at both ortho positions, providing a tetra-iodinated monomer, and the molecular weight is between about 1000 and 2000.

According to yet another embodiment, $R^1$ in formula (I) is selected from:

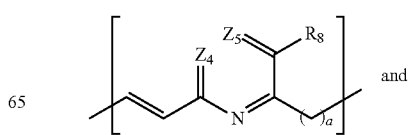

and

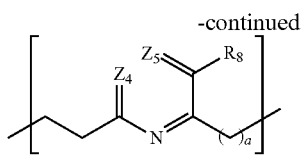

wherein $R^8$ is the same as described above with respect to formula (II); a and b range from 0 and 8, inclusive, and $Z^4$ and $Z^5$ are each independently O or S. According to more specific embodiments, a=1 and b=2.

Polymer embodiments include polycarbonates, polyarylates, polyiminocarbonates, polyphosphazenes and polyphosphoesters having the structure of formula (Ia),

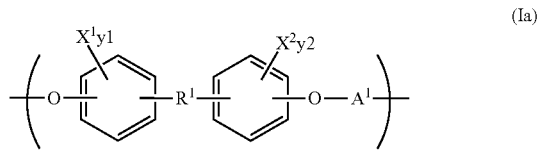

wherein $X^1$, $X^2$, y1, y2 and $R^1$, and the embodiments thereof, are the same as described above with respect to formula (I) and $A^1$ is selected from:

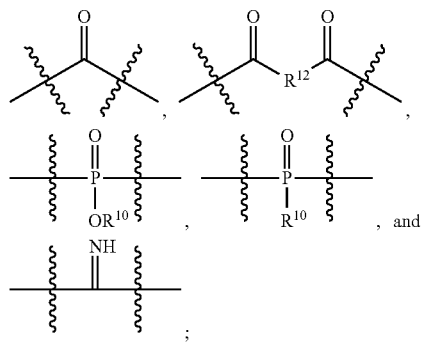

wherein $R^{10}$ is selected from H, $C_1$-$C_{30}$ alkyl, alkenyl or alkynyl and $C_2$-$C_{30}$ heteroalkyl; heteroalkenyl or heteroalkynyl, and $R^{12}$ is selected from $C_1$-$C_{30}$ alkyl, alkenyl or alkynyl, $C_1$-$C_{30}$ heteroalkyl; heteroalkenyl or heteroalkynyl, $C_5$-$C_{30}$ heteroalkylaryl, heteroalkenylaryl or heteroalkynylaryl, $C_6$-$C_{30}$ alkylaryl, alkenylaryl or alkynylaryl, and $C_5$-$C_{30}$ heteroaryl.

In an embodiment, $Q^1$ is a group having the structure:

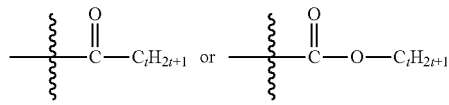

wherein t in the above groups is independently in the range of zero to about 18.

A polymer comprising a recurring unit of formula (I) can be copolymerized with any number of other recurring units. In an embodiment, the polymer comprising a recurring unit of formula (I) further comprises a recurring polyalkylene oxide block units of the formula (III):

 (III)

wherein B is —O—$((CHR^6)_p$—O$)_q$—; each $R^6$ is independently H or $C_1$ to $C_3$ alkyl; p is an integer ranging between about one and about four; q is an integer ranging between about five and about 3000; and $A^2$ is the same as $A^1$ in formula (Ia). One block copolymerized polymer embodiment contains a molar fraction of alkylene oxide between about 0.1 and about 25%. Another embodiment contains a molar fraction of alkylene oxide between about 0.5 and about 10%. Yet another embodiment contains a molar fraction of alkylene oxide between about 1 and about 5%.

Polymers can also be polymerized from diphenols corresponding to the structure of formula (I) prepared according to the methods disclosed by the above-referenced U.S. Pat. No. 5,099,060, the entire disclosure of which is incorporated herein by reference. The polymers can be copolymerized with diphenols that do not contain imine groups. Polymer embodiments are provided in which the molar fraction of imine repeating units monomer is between about 0.2 to about 85% by weight, preferably between about 13 to about 80% by weight, and more preferably between 20 and about 60% by weight. In another embodiment, conversion of amides to imines in the disclosed polymers is sufficient to reduce either glass transition temperature, melt viscosity or processing temperature by at least about 5%, preferably at least about 10%. Said conversion allows for at least a 30% decrease in $T_g$ and optimal processing temperatures.

Imine diphenol compounds thus represent new and useful compounds. Various embodiments are provided that are diphenol compounds with imine groups. One embodiment includes diphenol compounds having the structure of formula (IV):

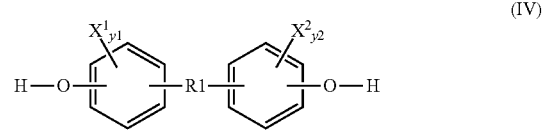

wherein $X^1$, $X^2$, y1, y2 and $R^1$, and the embodiments thereof, are the same as described above with respect to formula (I).

According to one diphenol embodiment, $R^1$ is selected so the formula (IV) monomer is an N-substituted di-tyrosine such as the N,N-dimethyl di-tyrosine depicted below formed by N-methylation of the di-tyrosine and/or is a 1,4-diazinedione (pyrazinedione) containing group monomeric unit in the forms depicted below:

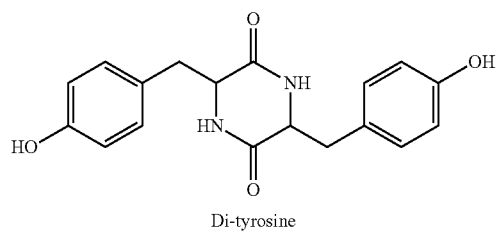

Di-tyrosine

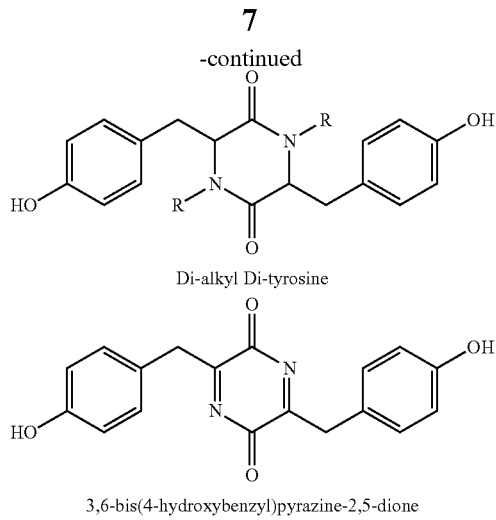

Di-alkyl Di-tyrosine 3,6-bis(4-hydroxybenzyl)pyrazine-2,5-dione

Di-tyrosines and their preparation are reported in the literature. Di-tyrosines can also be N-substituted by the procedures disclosed herein. The diazinedione (pyrazinedione) derivatives of said di-tyrosines are prepared by further and continued exposure of the di-tyrosines and/or the N-substituted derivatives to phosgene or triphosgene in the presence of pyridine. Upon adequate exposure of the di-tyrosine polymers to the extra phosgene or triphosgene, one of ordinary skill in the art can appreciate the formation of imine-containing derivatives of the di-tyrosine polymers.

N-substituted di-tyrosines can also be synthesized as shown in the scheme below:

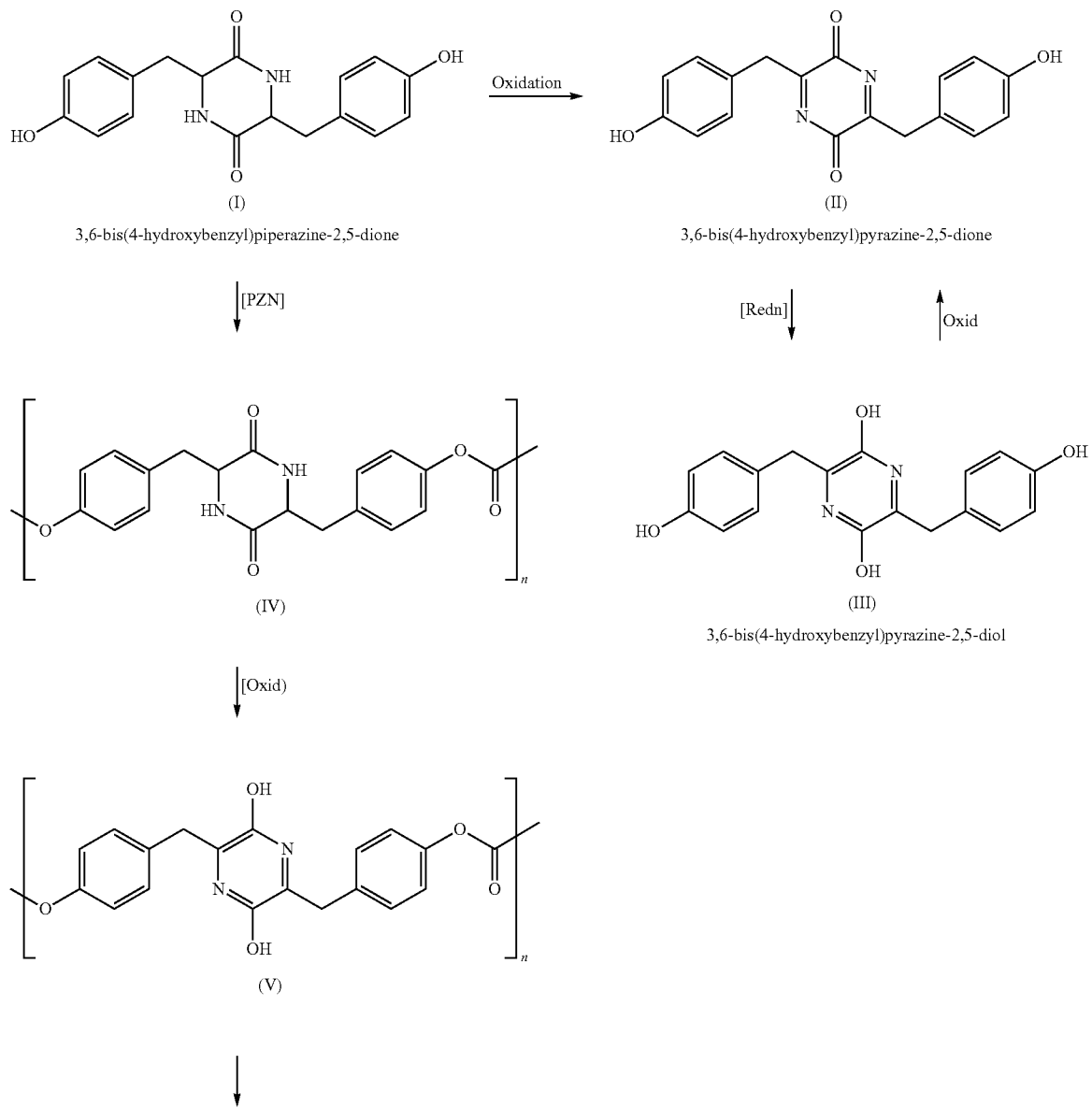

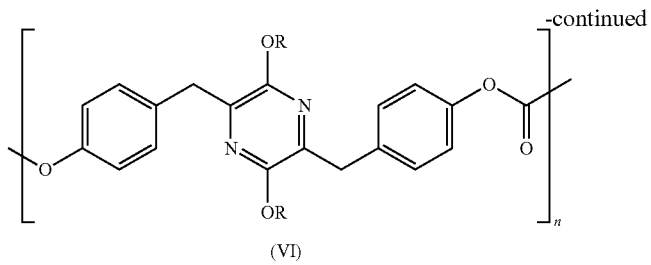

(VI)

A dehydrated dimer of tyrosine forms compound (I). Oxidation of 3,6-bis(4-hydroxybenzyl)piperazine-2,5-dione (I) to the corresponding 3,6-bis(4-hydroxybenzyl)pyrazine-2,5-dione (II) is then carried out. The diol intermediate (III) is an interesting compound from a materials standpoint and is the first oxidized compound from piperazinedione (I) enroute to pyrazinedione (II). Pyrazinedione (II) can also be reduced to the 3,6-bis(4-hydroxybenzyl)piperazine-2,5-diol (III). The last compound, diol (III), may provide a template for reaction, most especially, a side chain fatty acid synthesis through synthesis on pendent diol groups. The diol (III) is a highly symmetrical compound which leads to desirable polymeric properties.

In this scheme, the 3,6-bis(4-hydroxybenzyl)piperazine-2,5-dione (I) compound is polymerized and oxidized prior to introduction of compounds such as the side chain fatty acid onto the 3,6-bis(4-hydroxybenzyl)piperazine-2,5-diol (III). This work is analogous to a quinone-hydroquinone oxidative-reductive cycle. Pictorially, the drawing is as follows: Polymerization of 3,6-bis(4-hydroxybenzyl)piperazine-2,5-dione (I) with compounds such as bis(trichloromethyl) carbonate (triphosgene) forms (IV), followed by oxidation to form (V) and reaction with pendent alcohol groups in the presence of base such as pyridine or triethylamine and solvent such as dichloromethane, ethers, or acetonitrile, and other reactive functional groups such as alkyl halides or esters, on a fatty acid or other group would make it possible to synthesize compounds such as (VI).

In general, polymer embodiments disclosed herein possess excellent physical properties and melt processability and can be shaped into different three-dimensional structures for specific uses by conventional polymer-forming techniques such as extrusion and injection molding. The solvent-casting and compression molding techniques described in earlier patents disclosing polymers polymerized from tyrosine-derived diphenol compounds can also be used. Therefore, according to another embodiment, blood-contacting or tissue-implantable medical devices are provided, formed from the polymers disclosed herein. Preferably, the devices are formed by thermal fabrication. Such devices include hernia repair devices.

According to one embodiment, the medical device is a stent for treatment of a body lumen. Preferred stents are formed from or coated with the radio-opaque polymers disclosed herein, so that fluoroscopic imaging can be used to guide positioning of the device. A preferred radio-opaque, bioresorbable stent according to one embodiment is formed from a bioresorbable polymer with sufficient halogen atoms to render the stent inherently visible by X-ray fluoroscopy during stent placement.

According to another embodiment, the medical device is an embolotherapy product. Embolotherapy products are particulate formulations of biocompatible, bioresorbable polymers disclosed herein. In a preferred embodiment, the polymer contains a sufficient number of halogen atoms to render the embolotherapy product inherently radio-opaque.

Other specific applications for which the disclosed polymers are also particularly useful include scaffolds for tissue engineering on which isolated cell populations may be transplanted in order to engineer new tissues. The polymers are formed into porous devices as described by Mikos et al., Biomaterials, 14, 323-329 (1993) or Schugens et al., J. Biomed. Mater. Res., 30, 449-462 (1996) or U.S. Pat. No. 6,103,255 to allow for the attachment and growth of cells as described in Bulletin of the Material Research Society, Special Issue on Tissue Engineering (Guest Editor: Joachim Kohn), 21(11), 22-26 (1996). Therefore, another embodiment provides a tissue scaffold having a porous structure for the attachment and proliferation of cells either in vitro or in vivo formed from polymers disclosed herein.

Another specific application includes implantable drug delivery devices where a pharmaceutically active moiety is admixed within the polymeric matrix for slow release, including devices for ophthalmic drug delivery. Therefore, in one embodiment, the polymers are combined with a quantity of a biologically or pharmaceutically active compound sufficient to be therapeutically effective as a site-specific or systemic drug delivery system as described by Gutowska et al., J. Biomater. Res., 29, 811-21 (1995), and Hoffman, J. Controlled Release, 6, 297-305 (1987). Furthermore, another embodiment provides a method for site-specific or systemic drug delivery by implanting in the body of a patient in need thereof an implantable drug delivery device containing a therapeutically effective amount of a biologically or a physiologically active compound in combination with a polymer disclosed herein. Whenever a blood-contacting device is used for any length of time, the patient has to undergo anticoagulation therapy to prevent the formation of blood clots at the device surface. The acute thrombogenicity of artificial surfaces can be reduced by the release of a platelet aggregation inhibiting peptide drug from the device surface. Therefore, the polymeric drug formulation embodiments are provided containing an anti-thrombotic peptide drug can be used to form coatings on existing device surfaces by dipping or spray-coating techniques. Specific applications include the reformulation of the surface of vascular grafts, the formulation of new blood bags, and the reduction of the thrombogenic potential of tubings and membranes that come in contact with blood in extracorporeal devices.

Polymer embodiments may be prepared having good film-forming properties. An important phenomena observed for polymers having poly(alkylene oxide) block copolymer segments is the temperature-dependent phase transition of the polymer gel or the polymer solution in aqueous solvents. As the temperature increases, the polymer gel undergoes a phase transition to a collapsed state, while polymer solutions precipitate at a certain temperature or within certain temperature ranges. The polymers having poly(alkylene oxide) segments, and especially those that undergo a phase transition at about 30 to 40° C. on heating can be used as biomaterials for drug release and clinical implantation materials. Specific applications include films and sheets for the prevention of adhesion and tissue reconstruction.

Therefore, in another embodiment, poly(alkylene oxide) block copolymers of polymers disclosed herein may be formed into a sheet or a coating for application to exposed injured tissues for use as a barrier for the prevention of surgical adhesions as described by Urry et al., Mat. Res. Soc. Symp. Proc., 292, 253-64 (1993). Therefore, another embodiment provides a method for preventing the formation of adhesions between injured tissues by inserting as a barrier between the injured tissues a sheet or a coating of the radio-opaque poly(alkylene oxide) block copolymers of polymers disclosed herein.

The poly(alkylene oxide) segments decrease the surface adhesion of the polymers. As the molar fraction of poly(alkylene oxide) increases, the surface adhesion decreases. Polymer coatings containing poly(alkylene oxide) segments may thus be prepared that are resistant to cell attachment and are useful as non-thrombogenic coatings on surfaces in contact with blood. Such polymers also resist bacterial adhesion in this and in other medical applications as well. An embodiment is provided in which blood contacting devices and medical implants have surfaces coated with the poly(alkylene oxide) block copolymers disclosed herein.

The coated surfaces are preferably polymeric surfaces. Embodiments include methods that implant in the body of a patient a blood-contacting device or medical implant having a surface coated with the polymers disclosed herein containing poly(alkylene oxide) block copolymer segments.

By varying the molar fraction of poly(alkylene oxide) segments in the block copolymers, the hydrophilic/hydrophobic ratios of the polymers can be attenuated to adjust the ability of the polymer coatings to modify cellular behavior. Increasing levels of poly(alkylene oxide) inhibits cellular attachment, migration and proliferation, while increasing the amount of pendent free carboxylic acid groups promotes cellular attachment, migration and/or proliferation. Therefore, according to yet another embodiment, a method is provided for regulating cellular attachment, migration and/or proliferation by contacting living cells, tissues, or biological fluids containing living cells with the polymers disclosed herein.

Through pendant free carboxylic acid groups, derivatives of biologically and pharmaceutically active compounds, including drugs, can be attached to the polymer backbone by covalent bonds linked to the carboxylic acid pendent chain. This provides for the sustained release of the biologically or pharmaceutically active compound by means of hydrolysis of the covalent bond between the drug and the polymer backbone. Polymer embodiments are therefore also provided in which R is a biologically or pharmaceutically active compound covalently attached to the polymer backbone.

In addition, polymer embodiments containing pendent carboxylic acid groups have a pH dependent dissolution rate. This further enables the polymers to be used as coatings in gastrointestinal drug release carriers to protect some biologically and pharmaceutically active compounds such as drugs from degrading in the acidic environment of the stomach. The copolymer embodiments having a relatively high concentration of pendent carboxylic acid groups are stable and water insoluble in acidic environments but dissolve/degrade rapidly when exposed to neutral or basic environments. By contrast, copolymers of low acid to ester ratios are more hydrophobic and will not degrade/resorb rapidly in either basic or acidic environments. Therefore, another embodiment provides a controlled drug delivery system in which a biologically or pharmaceutically active agent is physically coated with a polymer disclosed herein having free carboxylic acid groups.

DETAILED DESCRIPTION OF PREFERRED EMBODIMENTS

The disclosed embodiments represent a novel class of monomers, and polymers polymerized therefrom, in which amino acids or amino acid structural derivatives are linked together to form new monomers and are then polymerized to form the new, useful polymers depicted in formula (I). The diphenol monomers of formula (IV) are prepared following standard procedures of peptide chemistry such as disclosed in J. P. Greenstein and M. Winitz, Chemistry of the Amino Acids, (John Wiley & Sons, New York 1961) and Bodanszky, Practice of Peptide Synthesis (Springer-Verlag, New York, 1984).

Specifically, carbodiimide-mediated coupling reactions in the presence of hydroxy-benzotriazole according to the procedures disclosed in U.S. Pat. No. 5,587,507 and U.S. Pat. No. 5,670,602, the disclosures of both of which are hereby incorporated by reference, are useful. Suitable carbodiimides are disclosed therein. The preferred carbodiimide is 1-ethyl-3-(3-dimethylamino-propyl)carbodiimide hydrochloride (EDCl.HCl). The crude monomers can be recrystallized twice, first from 50% acetic acid and water and then from a 20:20:1 ratio of ethyl acetate; hexane and methanol, or, alternatively, flash chromatography on silica gel is used, employing a 100:2 mixture of methylene chloride:methanol as the mobile phase.

Amide groups are converted to imine groups by exposure to phosgene or triphosgene and pyridine, causing the removal of acidic hydrogen and formation of the imino bond. The conversion is accomplished in one of three ways. Polymers with amide-containing repeating units are reacted with excess phosgene or triphosgene in a common solvent such as pyridine until at least partial conversion of amide bonds to imine bonds occur. Longer reaction times produce greater degree of bond conversion. The reaction is performed under ambient conditions.

Alternatively, monomers with amide bonds are converted by the same reaction to monomers with imine bonds and then subsequently polymerized to form polyimines. Lastly, monomers with amide bonds that polymerize by reaction with phosgene or triphosgene are reacted to form polyimines in a one-pot process using an excess amount of phosgene or triphosgene effective to carry the reaction beyond polymerization to formation of imine groups.

In one embodiment, the ratio of imine repeating units to amide repeating within the final polymer backbone ranges respectively from about 20 wt %-80 wt % to about 80 wt %-20 wt %, and in a preferred embodiment, said ratio is about 75% imine to 25% amide.

In another embodiment, imine-containing monomers can be derived from N-alkylated amide counterparts. There are several methods described in the scientific literature that accomplish such conversions. For example, the acidic hydrogens of amide groups can be replaced by alkyl groups in the monomer or polymer by reacting the monomer or polymer with paraformaldehyde followed by hydrogenation using $Pd/C/H_2$ or using sodium cyanoborohydride. The alkyl group can then be removed by methods known to those of ordinary skill in the art to form an imino double bond between the nitrogen and an adjacent carbon atom.

N-substituted monomers, their imine-containing monomeric counterparts, and the polymers of the present invention can also be prepared by substituting commercially-available N-substituted starting materials for the starting materials of monomers containing amide groups, such as the monomers disclosed by U.S. Pat. No. 5,099,060, using non-N-substituted starting materials and further dehydrogenation or dealkylation of the N atom of the monomeric unit.

Polymer embodiments can therefore contain a plurality of monomeric repeating units containing an imine or amide group, wherein the amide groups can be N-substituted, and the N-substituents and degree of N-substitution together with the number of amide groups replaced by imino groups are effective to render the polymer processable by a desired processing method. Preferably, a minimal amount of N-substituted monomer is used. This can range from one to three mole percent to render a non-soluble polymer soluble in a given solvent to up to about 25 mole percent to make the same polymer injection moldable. This can be readily determined by one of ordinary skill in the art without undue experimentation.

Imine-containing monomers can also be derived from thioamide monomers, prepared using the method described by A. Kjaer (Acta Chemica Scandinavica, 6, 1374-83 (1952)). The amide group in the monomers or polymers can also be converted to thioamide groups using the fluorous analog of the Lawesson's reagent ("FLR", or "f6LR") whose structure appears below (Kaleta, Z., et al., Org. Lett., 8(8), 1625-1628 (2006)). The second method is preferable, since it allows the formation of the monomer first then allows the conversion of the amide group to the thioamide group.

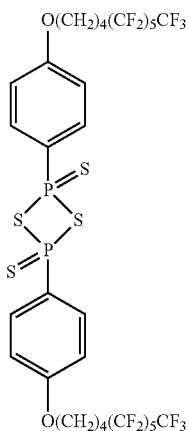

Fluorous Lawesson's Reagent (FLR)

Treatment of an amide with this reagent in 1:1 molar ratio in THF gives the corresponding thioamide in >88% yield after purification by chromatography or other means.

For the conversion of the tyrosine derived amide monomers to the corresponding thioamides, followed by conversion to the thio-imine, the phenolic groups of the monomers are first protected by converting them to the diacetyl esters as shown for diiodo-desaminotyrosyl tyrosine ethyl ester ($I_2$DTE) by treating with $Ac_2O$/pyridine. The O-protected $I_2$DTE is then reacted with FLR followed by base hydrolysis to the thioamide-$I_3$DTE as shown in the scheme. The transformation can also be carried out on the polymer using a similar procedure.

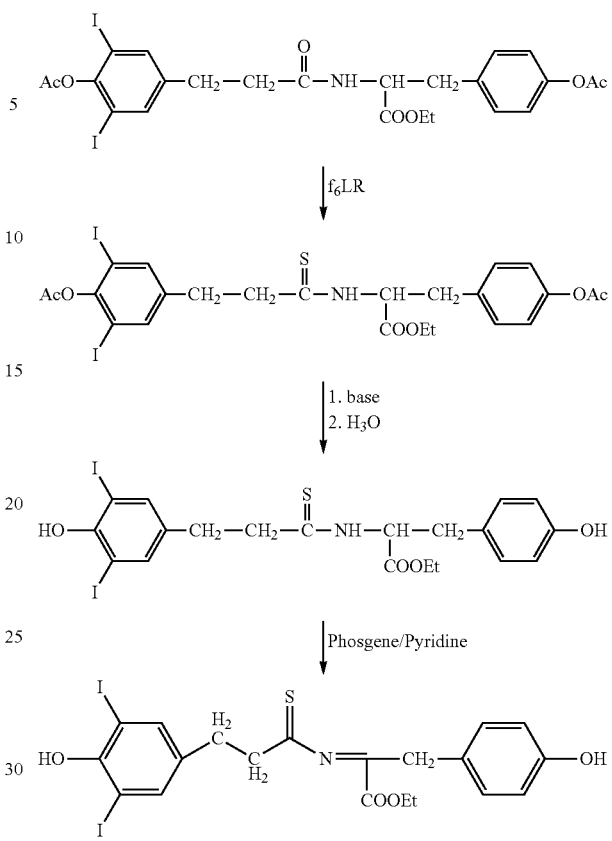

The thio-imine diphenol monomers of the present invention are formed by reacting the thioamide group with phosgene and pyridine to remove the acidic hydrogen, as depicted in the reaction scheme above.

Once the monomeric units having amide groups are formed, they can further be processed to remove the acidic hydrogen and converted to imine-containing monomeric units as depicted in the scheme above.

The N-substituted monomers, their imine-containing monomeric counterparts and the polymers of the present invention can be prepared by substituting commercially-available N-substituted starting materials for the starting materials of monomers containing amide groups, such as the monomers disclosed by U.S. Pat. No. 5,099,060, or by N-substituting monomers containing amide groups, such as the monomers prepared according to U.S. Pat. No. 5,099,060 using non-N-substituted starting materials and further dehydrogenation or dealkylation of the N atom of the monomeric unit.

There are several methods described in the scientific literature that can accomplish the formation of imine-containing monomers. For example, the acidic hydrogens of amide groups can be replaced by alkyl groups in the monomer by reacting the monomer or polymer with paraformaldehyde followed by hydrogenation using Pd/C/$H_2$ or using sodium cyanoborohydride. The alkyl group can then be removed by methods known to those of ordinary skill in the art to form a double bond between the N and its adjacent carbon atom.

In the alternative, the amide groups can simply be converted to imine groups by their further exposure to the precursors phosgene or triphosgene and pyridine, causing the removal of acidic hydrogen. It has been found convenient to react poly(amide carbonate) with excess phosgene or triphosgene in a common solvent such as pyridine until at least partial conversion of amide bonds to imine bonds occurs. Longer reaction times produce a greater degree of bond conversion.

Those having ordinary skill in the art, guided by the disclosure herein, can use the N-alkylation/N-arylation steps of forming a monomer precursor described herein to create any imine-containing monomer that corresponds to the polymers described above.

In another embodiment, the imino-monomer compounds are polymerized to form tissue-compatible bioerodable polymers for medical uses. Diphenol monomer embodiments can be used in any conventional polymerization process using diphenol monomers, including those processes that synthesize polymers traditionally considered hydrolytically stable and non-biodegradable.

This includes polyesters, polycarbonates, polyarylates, polyurethanes, polyphosphazines, polyphosphonates and polyethers, as well as random block copolymers of these polymers with poly(alkylene oxides) as described in U.S. Pat. No. 5,658,995, the disclosure of which is incorporated herein by reference.

In the presentation of the various polymer formulae, it is understood that the polymer structures as represented can also include homopolymers and heteropolymers, which can include stereoisomers. Homopolymer is used herein to designate a polymer comprised of all the same type of monomers. Heteropolymer is used herein to designate a polymer comprised of two or more different types of monomer, which is also called a co-polymer. A heteropolymer or co-polymer may be of a kind known as block, random and alternating. Further with respect to the presentation of the various polymer formulae, products according to embodiments disclosed herein may be comprised of a homopolymer, heteropolymer and/or a blend of such polymers.

The monomer compounds of formula (I) may also be reacted with phosgene to form polycarbonates with —O—C(=O)—O— linkages. The method is essentially conventional for polymerizing diols into polycarbonates. Suitable processes, associated catalysts and solvents are known in the art and are taught in Schnell, Chemistry and Physics of Polycarbonates, (Interscience, New York 1964), the teachings of which are also incorporated herein by reference. It is not necessary to use an imine-containing diphenol monomer. Monomeric repeating units will convert to imines by polymerization with excess phosgene or triphosgene.

Other methods adaptable for use in the preparation of polycarbonate polymer embodiments are disclosed in U.S. Pat. Nos. 6,120,491, and 6,475,477 the disclosures of which are incorporated herein by reference. Polycarbonates may also be prepared by dissolving the formula (I) monomer in methylene chloride containing 0.1M pyridine or triethylamine. A solution of phosgene in toluene at a concentration between about 10 and about 25 wt %, and preferably about 20 wt %, is added at a constant rate, typically over about two hours, using a syringe pump or other means. The reaction mixture is quenched by stirring with tetrahydrofuran (THF) and water, after which the polymer is isolated by precipitation with isopropanol (IPA). Residual pyridine (if used) can be conveniently removed by agitation of a THF polymer solution with a strongly acidic resin, such as AMBERLYST® 15.

The monomer compounds of formula (IV) may also be directly reacted with aliphatic or aromatic dicarboxylic acids in the carbodiimide-mediated process disclosed by U.S. Pat. No. 5,216,115 using 4-(dimethylamino) pyridinium-p-toluene sulfonate (DPTS) as a catalyst to form the aliphatic or aromatic poly(ester amides). The disclosure of U.S. Pat. No. 5,216,115 is incorporated by reference. This reaction requires the use of imine-containing monomer dicarboxylic acids, which according to one embodiment have the structure of formula (V):

(V)

in which, for the aliphatic copolymers, $R_5$ is selected from saturated and unsaturated, substituted and unsubstituted alkylene, arylene, arylalkylene or alkylarylene groups containing up to 18 carbon atoms, preferably 2 to 12 carbon atoms, and from 0 to 8 heteroatoms selected from O, S, N,N-loweralkyl, and P. For the aromatic copolymers, $R_5$ is selected from arylene, arylalkylene and alkylarylene groups containing up to 24 carbon atoms and preferably from 13 to 20 carbon atoms, and optionally may also include up to eight N, O, P or S atoms. The N-heteroatoms may be N-substituted to reduce polymer $T_g$ and melt viscosity.

The process forms polymers with —O—C(=O)—$R_5$—C(=O)—O— linkages. $R_5$ may be selected so that the dicarboxylic acids employed as the starting materials are either important naturally-occurring metabolites or highly biocompatible compounds. Aliphatic dicarboxylic acid starting materials therefore include the intermediate dicarboxylic acids of the cellular respiration pathway known as the Krebs Cycle. The dicarboxylic acids include α-ketoglutaric acid, succinic acid, fumaric acid and oxaloacetic acid ($R_5$ of formula (III) is —$CH_2$—$CH_2$—C(=O)—, —CH=CH— and —$CH_2$—C(=O)—, respectively).

Another naturally-occurring aliphatic dicarboxylic acid is adipic acid ($R_5$ is (—$CH_2$—)$_4$), found in beet juice. Still yet another biocompatible aliphatic dicarboxylic acid is sebacic acid ($R_5$ is (—$CH_2$—)$_8$), which has been studied extensively and has been found to be nontoxic as part of the clinical evaluation of poly(bis(p-carboxy-phenoxy)propane-co-sebacic acid anhydride) by Laurencin et al., J. Biomed. Mater. Res., 24, 1463-81 (1990).

Other biocompatible aliphatic dicarboxylic acids include oxalic acid ($R_5$ is a bond), malonic acid ($R_5$ is —$CH_2$—), succinic acid ($R_5$ is (—$CH_2$—)$_2$), glutaric acid ($R_5$ is (—$CH_2$—)$_3$), pimelic acid ($R_5$ is (—$CH_2$—)$_5$), suberic acid ($R_5$ is (—$CH_2$—)$_6$) and azelaic acid ($R_5$ is (—$CH_2$)$_7$). $R_5$ can thus represent (—$CH_2$—)$_Q$, wherein Q is between 0 and 8, inclusive. Among the suitable aromatic dicarboxylic acids are terephthalic acid, isophthalic acid and bis(p-carboxy-phenoxy) alkanes such as bis(p-carboxy-phenoxy) propane.

$R_5$ can also have the structure of formula (VI):

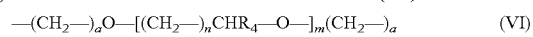
$$—(CH_2—)_aO—[(CH_2—)_nCHR_4—O—]_m(CH_2—)_a \quad (VI)$$

wherein a is from 1 to 3, inclusive, m is from 1 to 500,000, inclusive, and $R_4$ is hydrogen or a lower alkyl group containing from one to four carbon atoms. $R_4$ is preferably hydrogen, a is preferably 1, and m is preferably between about 10 and about 100, and more preferably between about 10 and about 50.

The diacids of formula (VI) are formed by the oxidation of poly(alkylene oxides) according to well-known methods. One example of such a compound is biscarboxymethyl poly (ethylene glycol), which is commercially available.

$R_5$ can also have the structure of formula (VII):

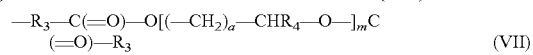
$$—R_3—C(=O)—O[(—CH_2—)_a—CHR_4—O—]_mC(=O)—R_3 \quad (VII)$$

wherein a, m and $R_4$ and the preferred species thereof are the same as described above with respect to formula (VI). $R_3$ is selected from a bond or straight and branched alkyl and alkylaryl groups containing up to 18 carbon atoms.

The dicarboxylic acids of formula (VII) are poly(alkylene oxides) bis-functionalized with dicarboxylic acids having the structure of formula (V) wherein $R_5$ is the same as described above for formula (V) and preferably contains up to 12 carbon atoms.

The poly(alkylene oxides) of formula (VII) that are bis-functionalized with dicarboxylic acid are prepared by the reaction of a non-functionalized poly(alkylene oxide) with an excess of either the dicarboxylic acid (mediated by a coupling agent such as dicyclohexyl carbodiimide), the anhydride (e.g. succinic anhydride) in the presence of pyridine or triethylamine, or a dicarboxylic acid chloride (e.g. adipoyl chloride) in the presence of an acid acceptor like triethylamine.

Polymers prepared from the formula (IV) monomeric starting materials with at least one bromine- or iodine-substituted aromatic ring are radio-opaque, such as the polymers prepared from radiopaque diphenol compounds prepared according to the disclosure of U.S. Pat. No. 6,475,477, as well as the disclosure of co-pending and commonly-owned U.S. patent application Ser. No. 10/952,202, the disclosures of both of which are incorporated herein by reference. The term "radiopaque" is used herein to designate an object or material comprising the object visible by in vivo analysis techniques for imaging such as, but not limited to, methods such as x-ray radiography, fluoroscopy, other forms of radiation, MRI, electromagnetic energy, structural imaging (such as computed or computerized tomography), and functional imaging (such as ultrasonography). The iodinated and brominated diphenol monomers can also be employed as radio-opacifying, biocompatible non-toxic additives for other polymeric biomaterials.

Bromine and iodine substituted aromatic monomer embodiments are prepared by well-known iodination and bromination techniques that can be readily employed by those of ordinary skill in the art guided by the above referenced granted patent and pending application (now published) without undue experimentation. The halogenated aromatic compounds from which the halogenated aromatic monomers are prepared undergo ortho-directed halogenation. The term, "ortho-directed", is used herein to designate orientation of the halogen atom(s) relative to the hydroxyl group of the phenoxy.

Random or block copolymers of the formula (I) polymer embodiments with a poly(alkylene oxide) may be prepared according to the method disclosed in U.S. Pat. No. 5,658,995, the disclosure of which is also incorporated by reference. The poly(alkylene oxide) is preferably a poly(ethylene glycol) block/unit typically having a molecular weight of less than about 10,000 per unit. More typically, the poly(ethylene glycol) block/unit has a molecular weight less than about 4000 per unit. The molecular weight is preferably between about 1000 and about 2000 per unit.

The molar fraction of poly(ethylene glycol) units in block copolymers may range from greater than zero to less than 1, and is typically greater than zero up to about 0.5, inclusive. More preferably, the molar fraction is less than about 0.25 and yet more preferably, less than about 0.1. In more preferred embodiments, the molar fraction may vary from greater than about 0.001 to about 0.08, and most preferably, between about 0.025 and about 0.035.

Unless otherwise indicated, the molar fractions reported herein are based on the total molar amount of poly(alkylene glycol) and non-glycol units in the polymers Applicants have also recognized that the polymer glass transition temperature increases as the degree of halogenation and the molar fraction of free carboxylic acid units increases. Higher weight percentages of poly(alkylene oxide) are typically used in polymers with higher levels of iodination and/or with higher molar fractions of free carboxylic acid units to maintain the polymer glass transition temperature within a desired range for the end use application. N-alkylation and/or conversion of amide to imine linkages within the monomeric units provides an alternative means for lowering the polymer glass transition temperature so that the amount of poly(alkylene oxide) may be lowered or eliminated without adversely affecting the polymer melt properties. More tools are therefore placed at the disposal of the polymer chemist for fine-tuning the physico-mechanical properties of polymers.

The formula (I) polymers have weight-average molecular weights above about 20,000, and preferably above about 80,000, as determined from gel permeation chromatography (GPC) relative to polystyrene standards using tetrahydrofuran (THF) as the eluent, without further correction.

Polymer embodiments are defined as including polymers polymerized from formula (IV) monomers having pendent free carboxylic acid groups ($R_8$=OH). However, it is not possible to polymerize polymers having pendent free carboxylic acid groups from corresponding monomers with pendent free carboxylic acid groups without cross-reaction of the free carboxylic acid group with the co-monomer. Accordingly, polymer embodiments are provided having pendent free carboxylic acid groups are prepared from homopolymers and copolymers of benzyl and tert-butyl ester monomer embodiments having the structure of formula (IV) in which $R_8$ is a benzyl or tert-butyl group.

The benzyl ester homopolymers and copolymers may be converted to corresponding free carboxylic acid homopolymers and copolymers through the selective removal of the benzyl groups by the palladium catalyzed hydrogenolysis method disclosed by co-pending and commonly owned U.S. Pat. No. 6,120,491, the disclosure of which is incorporated herein by reference.

The tert-butyl ester homopolymers and copolymers may be converted to corresponding free carboxylic acid homopolymers and copolymers through the selective removal of the tert-butyl groups by the acidolyis method disclosed by the above-referenced U.S. patent application Ser. No. 10/952, 202, also incorporated herein by reference.

The catalytic hydrogenolysis or acidolysis is necessary because the liability of the polymer backbone prevents the employment of harsher hydrolysis techniques.

Applicants have recognized that the molar fraction of free carboxylic acid units in the polymers can be adjusted to influence the degradation/resorbability of devices made from such polymers. For example, applicants have recognized that while poly(DTE-co-35 mol % DT carbonate), (a tyrosine-derived polycarbonate comprising about 35% free carboxylic acid units) is 90% resorbed in about 15 days, polycarbonates with lower amounts of free carboxylic acid will have desirably longer lifetimes in the body. Furthermore, by otherwise adjusting the amount of free carboxylic acid in the polymers across the range of preferred molar fraction, the resulting polymers can be adapted for use in various applications requiring different device lifetimes. In general, the higher the molar fraction of free carboxylic acid units, the shorter the lifetime of the device in the body and more suitable such devices are for applications wherein shorter lifetimes are required. In certain embodiments where lifetimes of 6 months or more are required, polymers of the presently preferred ranges of free carboxylic acid units tend to be desirable.

After polymerization, appropriate work up of the disclosed polymers may be achieved by any of a variety of known methods commonly employed in the field of synthetic polymers to produce a variety of useful articles with valuable physical and chemical properties, all derived from tissue-compatible monomers. The useful articles can be shaped by conventional polymer-forming techniques such as extrusion, compression molding, injection molding, solvent casting, spin casting, wet spinning, combinations of two or more thereof, and the like. Shaped articles prepared from the polymers are useful, inter alia, as degradable biomaterials for medical implant applications. Such applications include the use of shaped articles as vascular grafts and stents.

Stent fabrication processes may further include two-dimensional methods of fabrication such as cutting extruded sheets of polymer, via laser cutting, etching, mechanical cutting, or other methods, and assembling the resulting cut portions into stents, or similar methods of three-dimensional fabrication of devices from solid forms. In certain other embodiments, the polymers are formed into coatings on the surface of an implantable device, particularly a stent, made either of a polymer disclosed herein or another material, such as metal. Such coatings may be formed on stents via techniques such as dipping, spray coating, combinations thereof, and the like. Further, stents may be comprised of at least one fiber material, curable material, laminated material, and/or woven material. Details of stern products and fabrication in which the polymers disclosed herein may be employed are disclosed in co-pending and commonly-owned U.S. patent application Ser. No. 10/952,202 filed Sep. 27, 2004, the disclosure of which is incorporated by reference. Sterns are preferably fabricated from the radiopaque polymers disclosed herein, to permit fluoroscopic positioning of the device.

The highly beneficial combination of properties associated with the polymer embodiments disclosed herein are well-suited for use in producing a variety of medical devices besides stents, especially implantable medical devices that are preferably radiopaque, biocompatible, and have various times of bioresorption. For example, applicants have recognized that, in certain embodiments, the polymers are suitable for use in producing implantable devices for orthopedics, tissue engineering, dental applications, wound closure, gastric lap bands, drug delivery, cancer treatment, other cardiovascular applications, non-cardiovascular stents such as biliary, esophagus, vaginal, lung-trachea/bronchus, and the like. In addition, the polymers are suitable for use in producing implantable, radiopaque discs, plugs, and other devices used to track regions of tissue removal, for example, in the removal of cancerous tissue and organ removal, as well as, staples and clips suitable for use in wound closure, attaching tissue to bone and/or cartilage, stopping bleeding (homeostasis), tubal ligation, surgical adhesion prevention, and the like. Applicants have also recognized that the polymers disclosed herein are well-suited for use in producing a variety of coatings for medical devices, especially implantable medical devices.

Furthermore, in some preferred embodiments, the present polymers may be advantageously used in making various orthopedic devices including, for example, radiopaque biodegradable screws (interference screws), radiopaque biodegradable suture anchors, and the like for use in applications including the correction, prevention, reconstruction, and repair of the anterior cruciate ligament (ACL), the rotator cuff/rotator cup, and other skeletal deformities.

Other devices, which can be advantageously formed from the polymers disclosed herein, include devices for use in tissue engineering. Examples of suitable devices include tissue engineering scaffolds and grafts (such as vascular grafts, grafts or implants used in nerve regeneration). The present polymers may also be used to form a variety of devices effective for use in closing internal wounds. For example, biodegradable sutures, clips, staples, barbed or mesh sutures, implantable organ supports, and the like, for use in various surgery, cosmetic applications, and cardiac wound closures can be formed.

Various devices finding use in dental applications may advantageously be formed according to preferred aspects of the presently disclosed polymer embodiments. For example, devices for guided tissue regeneration, alveolar ridge replacement for denture wearers, and devices for the regeneration of maxilla-facial bones may benefit from being radiopaque so that the surgeon/dentist can ascertain the placement and continuous function of such implants by simple X-ray imaging.

The present polymers are also useful in the production of gastric lap bands for use in the treatment of obesity. The production of radiopaque lap bands allows for more effective monitoring of the devices in the human body, and more effective treatment of obesity.

In addition to intravascular stents and non-cardiovascular stents, the present polymers are useful in a number of other cardiovascular and vascular devices. For example, valves, chordae tendinea replacements, annuloplasty rings, leaflet repair patches, vascular grafts, vascular tubes, patches for septal defects, arterial and venous access closure devices (plugs), and the like can be formed for use in replacement repair of heart valves, tubes, and the like. In addition, portions of an artificial heart, such as the rough surface/fibroid layer (bellow pumps) may be formed from the polymer embodiments described herein.

Polymer embodiments are provided that are also useful in the production of bioresorbable, inherently radiopaque polymeric embolotherapy products for the temporary and therapeutic restriction or blocking of blood supply to treat tumors and vascular malformations, e.g., uterine fibroids, tumors (i.e., chemoembolization), hemorrhage (e.g., during trauma with bleeding) and arteriovenous malformations, fistulas and aneurysms delivered by means of catheter or syringe. Details of embolotherapy products and methods of fabrication in which the polymers disclosed herein may be employed are disclosed in co-pending and commonly-owned U.S. patent application Ser. No. 10/952,274 filed Sep. 27, 2004, the disclosure of which is incorporated by reference. Embolotherapy treatment methods are by their very nature local rather than systemic and the products are preferably fabricated from the radiopaque polymers disclosed herein, to permit fluoroscopic monitoring of delivery and treatment.

Accordingly, at least one embodiment is disclosed directed to a composition comprising a biocompatible polymer, a biocompatible contrast agent, and a biocompatible solvent which solubilizes said biocompatible polymer as a delivery vehicle, wherein sufficient amounts of said polymer are employed in said composition such that, upon delivery to a vascular site, a polymer can precipitate and embolizes the site of interest.

While a preferred embodiment has been described above, a number of variations and modifications may suggest themselves to those skilled in the pertinent arts. For example, those of ordinary skill in the art can appreciate the composition and/or implant device for each patient in a variety of "standard" quantity, sizes and shapes may be made.

The present polymers are further useful in the production of a wide variety of therapeutic agent delivery devices. Such devices may be adapted for use with a variety of therapeutics including, for example, pharmaceuticals (i.e., drugs) and/or biological agents as previously defined and including biomolecules, genetic material, and processed biologic materials, and the like. Any number of transport systems capable of delivering therapeutics to the body can be made, including devices for therapeutics delivery in the treatment of cancer, intravascular problems, dental problems, obesity, infection, and the like.

In certain embodiments, any of the aforementioned devices described herein can be adapted for use as a therapeutic delivery device (in addition to any other functionality thereof). Controlled therapeutic delivery systems may be prepared, in which a therapeutic agent, such as a biologically or pharmaceutically active and/or passive agent, is physically embedded or dispersed within a polymeric matrix or physically admixed with a polymer disclosed herein. Controlled therapeutic agent delivery systems may also be prepared by direct application of the therapeutic agent to the surface of an implantable medical device such as a bioresorbable stein device (comprised of at least one of the present polymers) without the use of these polymers as a coating, or by use of other polymers or substances for the coating.

Pendant carboxylic acid groups of polymers may also be derivatized by the covalent attachment of a therapeutic agent. Depending upon the moieties present on the underivatized therapeutic agent, the covalent bond may be an amide bond or an ester bond. Typically, the therapeutic agent is derivatized at a primary or secondary amine, hydroxyl, ketone, aldehyde or carboxylic acid group. Chemical attachment procedures are described by U.S. Pat. Nos. 5,219,564 and 5,660,822; Nathan et al., Bio. Cong. Chem., 4, 54-62 (1993) and Nathan, Macromolecules, 25, 4476 (1992), the disclosures of which are incorporated by reference. The therapeutic agent may first be covalently attached to a monomer, which is then polymerized, or the polymerization may be performed first, followed by covalent attachment of the therapeutic agent.

Hydrolytically stable conjugates are utilized when the therapeutic agent is active in conjugated form. Hydrolyzable conjugates are utilized when the therapeutic agent is inactive in conjugated form.

Therapeutic agent delivery compounds may also be formed by physically blending the therapeutic agent to be delivered with the polymers disclosed herein using conventional techniques well-known to those of ordinary skill in the art. For this therapeutic agent delivery embodiment, it is not essential that the polymer have pendent groups for covalent attachment of the therapeutic agent.

The disclosed polymer compositions containing therapeutic agents, regardless of whether they are in the form of polymer conjugates or physical admixtures of polymer and therapeutic agent, are suitable for applications where localized delivery is desired, as well as in situations where a systemic delivery is desired. The polymer conjugates and physical admixtures may be implanted in the body of a patient in need thereof, by procedures that are essentially conventional and well-known to those of ordinary skill in the art.

Implantable medical devices may thus be fabricated that also serve to deliver a therapeutic agent to the site of implantation by being fabricated from or coated with the therapeutic agent delivery system in which a polymer disclosed herein has a therapeutic agent physically admixed therein or covalently bonded thereto, such as a drug-eluting stent. Embolotherapeutic particles may also be fabricated for delivery of a therapeutic agent.

Examples of biologically or pharmaceutically active therapeutic agents that may be covalently attached to the polymers disclosed herein include acyclovir, cephradine, malphalen, procaine, ephedrine, adriamycin, daunomycin, plumbagin, atropine, quinine, digoxin, quinidine, biologically active peptides, chlorin e.sub.6, cephradine, cephalothin, proline and proline analogs such as cis-hydroxy-L-proline, malphalen, penicillin V, aspirin and other non-steroidal anti-inflammatories, nicotinic acid, chemodeoxycholic acid, chlorambucil, anti-tumor and anti-proliferative agents, including anti-proliferative agents that prevent restenosis such as rapamycin or cyclosporin, hormones such as estrogen, and the like. Biologically active compounds are additionally defined as including cell attachment mediators, biologically active ligands, and the like.

In yet another embodiment, Polymeric drug formulations are described. According to this aspect of the invention suitable pharmaceutically active compounds such as platelet aggregation inhibiting peptide drugs are formulated in a controlled release site specific polymeric delivery system. Therefore, methods for site-specific drug delivery in accordance with the present invention are also provided.

The polymer-therapeutic agent combination embodiments may also be formed into shaped particles, such as valves, stents, tubing, prostheses, and the like.

Therapeutically effective dosages may be determined by either in vitro or in vivo methods. For each particular compound, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate from the formulations disclosed herein are also varied within the routine skill in the art to determine an advantageous profile, depending on the therapeutic conditions to be treated.

A typical dosage might range from about 0.001 mg/k/g to about 1,000 mg/k/g, preferably from about 0.01 mg/k/g to about 100 mg/k/g, and more preferably from about 0.10 mg/k/g to about 20 mg/k/g. Advantageously, the compounds disclosed herein may be administered several times daily, and other dosage regimens may also be useful.

In practicing the method embodiments, the polymer-therapeutic agent combinations may be used alone or in combination with other therapeutic or diagnostic agents. The compounds disclosed herein can be utilized in vivo, ordinarily in mammals such as primates such as humans, sheep, horses, cattle, pigs, dogs, cats, rats and mice, or in vitro.

The following non-limiting examples set forth herein below illustrate certain of the disclosed embodiments. All parts and percentages are by mole percent unless otherwise noted and all temperatures are in degrees Celsius unless otherwise indicated. All solvents were HPLC grade and all other reagents were of analytical grade and were used as received, unless otherwise indicated.

EXAMPLES

Example 1

Preparation of Acyl-Imine-Containing Polycarbonates By Reacting Monomer With Excess Triphosgene In a 500 mL round bottomed flask were placed 15 g (0.042 mol) of desaminotyrosyl tyrosine ethyl ester (DTE) 0.011 g (0.07 mmol) of ethyl 4-hydroxybenzoate (endcapping agent), 12.45 g (0.16 mol) of pyridine, and 150 mL of methylene chloride and stirred under a nitrogen atmosphere. Triphosgene (6.65 g, 0.067 mol of phosgene) was dissolved in 37 mL of methylene chloride and the solution was added to the flask using a syringe pump over a 2 h period. After the addition was complete the reaction mixture was stirred for 17 h. The reaction mixture was precipitated with 1 L of 2-propanol in a 4L blender. The resulting gel like product was ground repeatedly with 0.5 L of 2-propanol. The solid product was isolated by filtration and ground with Deionized water and finally dried in a vacuum oven. $^1$H NMR indicated a ratio of 2:1 of imine (—C=N—) to amide (—CH—NH—).

Example 2

Preparation of an Acyl-Imine-Containing Polycarbonate

In a 250 mL round bottomed flask were placed 10 g of poly(DTE carbonate) (PDTEC; 0.026 mol repeat units), pyridine (2.57 g, 0.026 mol), and 100 mL of methylene chloride. To the resulting solution was added with stirring a solution of triphosgene (1.29 g, 0.013 mol of phosgene) in 5 mL of methylene chloride over a 90 min period. The reaction mixture was stirred at ambient temperature for 24 h and then precipitated with 500 mL of 2-propanol in a blender. The resulting yellow polymer was washed twice with 250 mL portions of 2-propanol, isolated by filtration and dried in vacuum oven at 40° C. The polymer was characterized by $^1$H NMR, and gel permeation chromatography. $^1$H NMR indicated that 30% of the —CH—NH— groups had been converted to —C=N— groups.

Example 3

Preparation of Imine-DTE Monomer

This monomer was prepared by de-polymerization of a copolymer containing 60% DTE 40% imine-DTE prepared as described in the examples above. To 10.5 g (28.7 mmol of repeat units) of the copolymer in a 500 mL Erlenmeyer flask were added 75 mL of 95% ethanol, 100 mL of water and 6 g (150 mmol) of sodium hydroxide. The mixture was stirred at ambient temperature for 6 h when a clear, orange-brown solution resulted. The flask was cooled in ice-water bath and 15 mL of 12 M aqueous HCl was added with stirring. A viscous brown oil separated. The oil was dissolved in 20 mL of tetrahydrofuran and the solution was stirred with 60 mL of saturated aqueous NaHCO$_3$ solution for 5 minutes and allowed stand, whereupon two layers were formed. The bottom oily layer was extracted 3 times with 10 mL each of saturated aqueous NaHCO$_3$ solution. The viscous oil was finally stirred with 50 mL deionized water until an off-white solid separated. The product was isolated by filtration and washed with water and then dried in a vacuum oven at 40° C., which gave 3 g of the imine-DTE. The product was characterized by $^1$H NMR spectroscopy, elemental analysis, and hplc (high performance liquid chromatography).

Example 4

Preparation of Poly(Imine-DTE Carbonate)

In a 50 mL 3-necked flask with an overhead stirrer were placed 2 g (5.6 mmol) of imine-DTE, 15 mL of methylene chloride and 2 g (25 mmol) of pyridine. A clear solution formed on stirring. Triphosgene (0.8 g, 8 mmol of phosgene) was dissolved in 8 mL of methylene chloride and added to the reaction flask over 2 hours using a syringe pump. The reaction mixture was stirred for 15 minutes and then quenched by stirring with 20 mL of water. After removal of the top layer the organic layer was washed twice with 20 mL of water. The polymer solution was then precipitated with 30 mL of 2-propanol (IPA). The resulting viscous oil was hardened by further precipitation with IPA.

The product was dried in a vacuum oven at 50° C. for 24 h. The polymer had a polystyrene equivalent MW of 53 Kda, a T$_g$ of 57° C. (by comparison Tg of poly(DTE carbonate is 95° C.) and its $^1$H NMR spectrum was in agreement with the structure.

It will be understood by those of skill in the art that numerous and various modifications can be made without departing from the spirit of the present invention. Therefore, it should be clearly understood that the various embodiments of the present invention described herein are illustrative only and not intended to limit the scope of the present invention.

What is claimed is:

1. In a biocompatible, bioresorbable polymer comprising a plurality of amide-containing monomeric repeating units, wherein the improvement comprises replacing at least 20 weight percent of the amide groups in said amide-containing monomeric repeating units with carbonyl-imine groups, and wherein said polymer is a heteropolymer or a copolymer characterized by one or more repeating units of the formula:

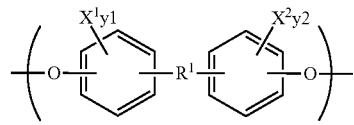

wherein X$^1$ and X$^2$ are each independently selected from Br and I; y1 and y2 are each independently zero or an integer in the range of 1 to 4, and R$^1$ is selected from the group consisting of:

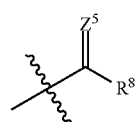

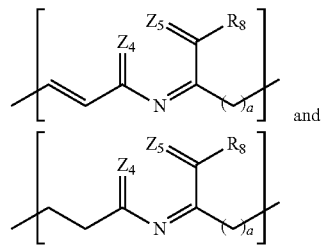

wherein Z$^4$ is O or S; Z$^5$ is O or S; a and b independently range between 0 and 8, inclusive; and R$^8$ is selected from the group consisting of OH, a poly(alkylene oxide), O—(C$_1$-C$_{18}$ alkyl), O-alkenyl O-alkynyl and O-cycloalkyl.

2. The polymer according to claim 1, wherein at least one aromatic ring of formula (I) is substituted with iodine, so that the sum of y1 and y2 in formula (I) is greater than zero.

3. The polymer according to claim 1, comprising repeating units in which $R^8$ is OH.

4. In a biocompatible, bioresorbable polymer comprising a plurality of amide-containing monomeric repeating units, wherein the improvement comprises replacing at least 20 weight percent of the amide groups in said amide-containing monomeric repeating units with carbonyl-imine groups, and wherein said polymer is a heteropolymer characterized by being a polycarbonate, polyarylate, polyphosphazene or polyphosphoester having one or more repeating units of formula (Ia):

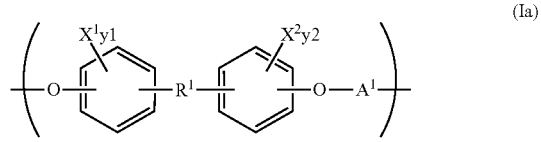

wherein $X^1$ and $X^2$ are each independently selected from Br and I; y1 and y2 are each independently zero or an integer in the range of 1 to 4, and $R^1$ is selected from the group consisting of:

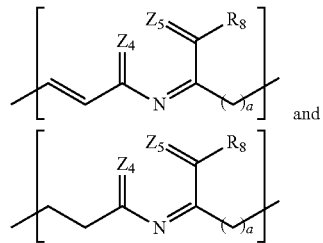

wherein $Z^4$ is O or S; $Z^5$ is O or S; a and b independently range between 0 and 8, inclusive; $R^8$ is selected from the group consisting of OH, a poly(alkylene oxide), O—($C_1$-$C_{18}$ alkyl), O-alkenyl, O-alkynyl, and O-cycloalkyl; and wherein $A^1$ is selected from the group consisting of:

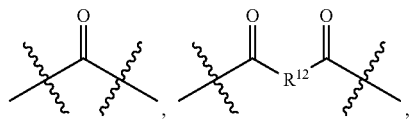

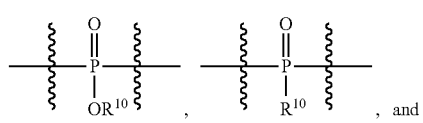

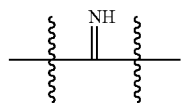

wherein $R^{10}$ is selected from H, $C_1$-$C_{30}$ alkyl, alkenyl or alkynyl and $C_2$-$C_{30}$ heteroalkyl; heteroalkenyl or heteroalkynyl; and $R^{12}$ is selected from $C_1$-$C_{30}$ alkylene, alkenylene or alkynylene; $C_1$-$C_{30}$ heteroalkylene, heteroalkenylene or heteroalkynylene; $C_5$-$C_{30}$ heteroalkylarylene, heteroalkenylaryene or heteroalkynylarylene; $C_6$-$C_{30}$ alkylarylene, alkenylarylene or alkynylarylene; and $C_5$-$C_{30}$ heteroarylene.

* * * * *